United States Patent [19]

Jennings

[11] Plant 4,424

[45] Jun. 12, 1979

[54] TAYBERRY

[75] Inventor: Derek L. Jennings, Dundee, Scotland

[73] Assignee: National Seed Development Organisation Limited, Cambridge, England

[21] Appl. No.: 874,011

[22] Filed: Jan. 31, 1978

[51] Int. Cl.[2] ..... A01H 5/03

[52] U.S. Cl. ..... Plt./46

[58] Field of Search ..... Plt./46

*Primary Examiner*—Robert E. Bagwill

*Attorney, Agent, or Firm*—Burns, Doane, Swecker & Mathis

[57] ABSTRACT

The invention relates to a new and distinct hybrid Rubus variety which has been designated the Tayberry. The subject variety was formed by the crossing of the octoploid blackberry Aurora with a tetraploid raspberry pollen parent known as 626/67. This variety resembles the Loganberry in some respects, but is superior to it with respect to fruit size, yield, fruit color, mode of presentation of fruit, and ease of propagation by root cuttings.

5 Drawing Figures

SUMMARY OF THE INVENTION

The original plant was selected from a family of seedlings resulting from a cross made in 1969 at the Scottish Horticultural Research Institute, Dundee, UK, between the octoploid blackberry Aurora and a tetraploid raspberry. Aurora, which was bred at Corvallis, Oregon, served as the maternal parent. The pollen parent was 626/67, a tetraploid raspberry also bred at the Scottish Horticultural Research Institute. The family resulting from this cross was designated 69102.

The present variety, which has been designated the Tayberry, resembles the Loganberry is some respects, but is superior to it with respect to fruit size, yield, fruit color, mode of presentation of fruit, and ease of propagation by root cuttings.

The performance of the new variety has been evaluated in trials at the Scottish Horticultural Research Institute; the National Fruit Trials at Faversham, England; and elsewhere in the UK. Continuous asexual propagation has demonstrated that its characteristics are stable and are transmitted without change through succeeding propagations. The variety may be reproduced with ease by leaf-bud cuttings and by suckers produced in a spawn-bed.

BRIEF DESCRIPTION OF THE DRAWINGS

The accompanying drawings show typical specimens of the new variety in color as nearly true as is reasonably possible to make the same in a color illustration of this character. In each instance the photographs were made at the Scottish Horticultural Research Institute, Dundee, UK.

DETAILED DESCRIPTION

Figure 1:
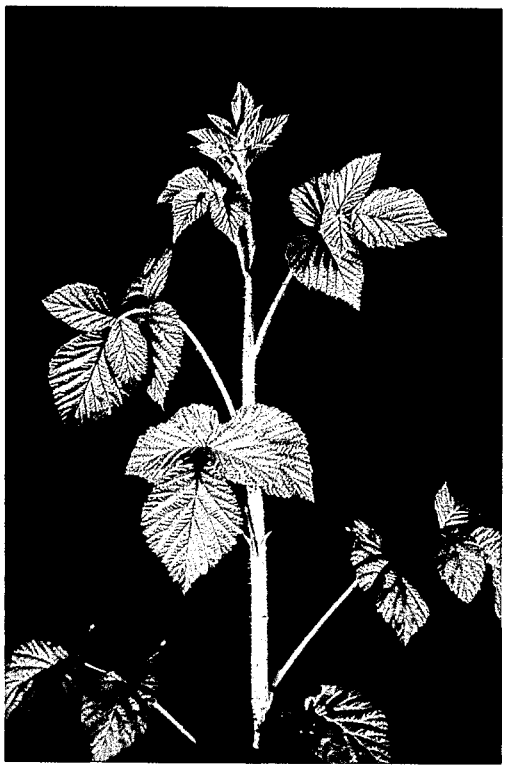
FIG. 1 is a young shoot tip of Tayberry photographed in May 1977.
Figure 2:
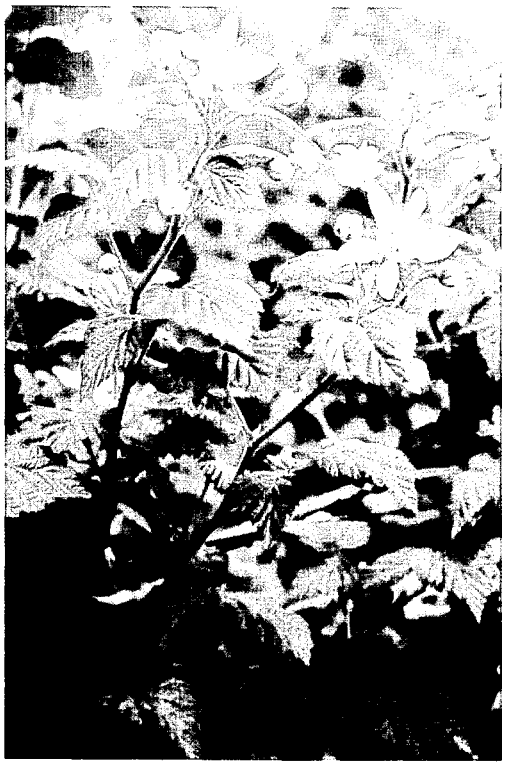
FIG. 2 is a flowering lateral of Tayberry photographed in June 1977.
Figure 3:
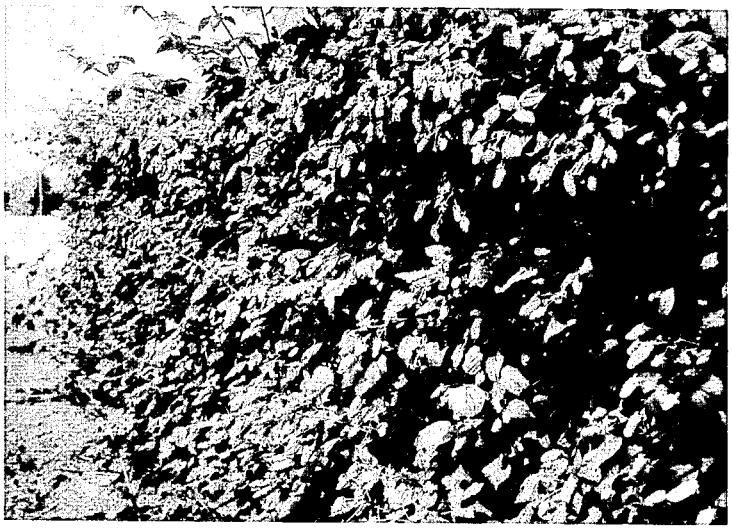
FIG. 3 is a row of Tayberry planted during 1973 and photographed in July 1976.
Figure 4:
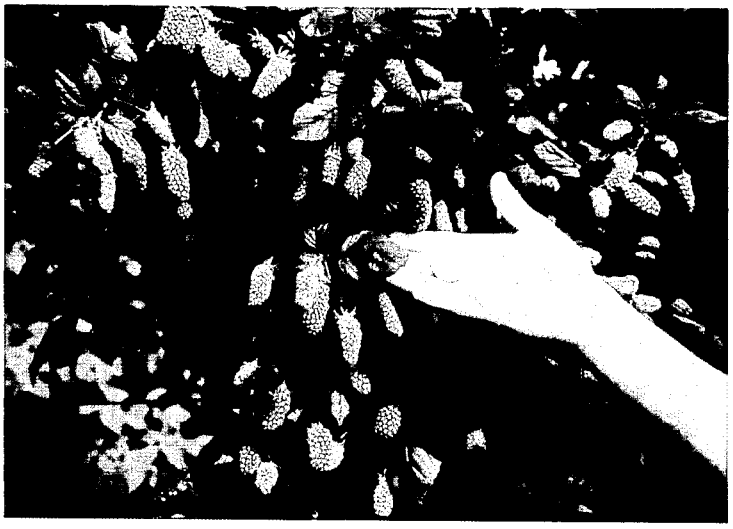
FIG. 4 is a closer view of a portion of the row of FIG. 3.
Figure 5:
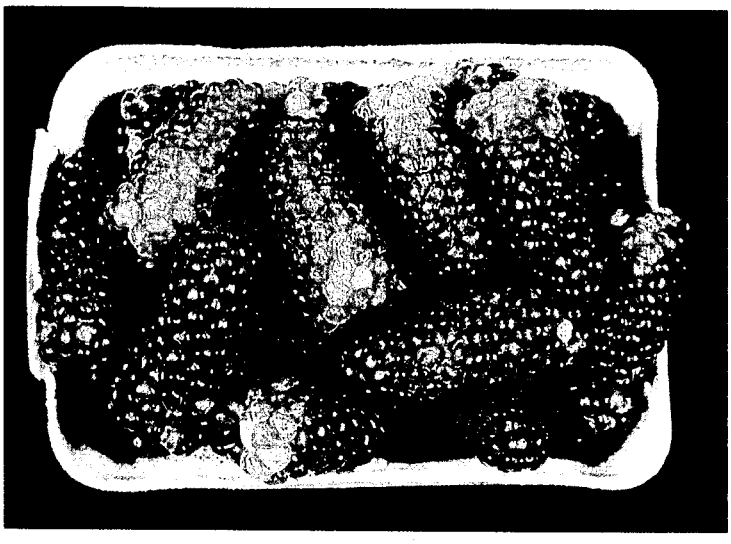
FIG. 5 is a punnet of Tayberry fruits prior to full ripening photographed in July 1976. (The fully ripe fruits are a deeper purple than illustrated in FIG. 5.)

The following is a detailed description of the new variety's characteristics as observed at the Scottish Horticultural Research Institute. Color terminology employed is to be accorded its ordinary dictionary significance. As will be apparent to those skilled in horticultural science, the colors of the leaves and stems vary with the stage of growth and are useful only for general guidance. Similarly, the fruit color varies with the stage of ripeness.

Description of One Year Old Vegetative Shoots

Vigorous, sturdy shoots, spreading in young plants but later tending towards a more semi-erect habit. Spines are dense, elliptical in shape and highly pigmented at their base and tip. Leaves are a deep green but red pigmentation is prominent, especially in young leaves, around the margins of older leaves and in the petioles. The leaflets are very slightly convex, usually five in number and have a distinct relief between the veins. Suckering in the true botanical sense does not occur, but established plants commonly produce from approximately 5 to 9 replacement canes from root-stock buds.

GENERAL HABIT

Strength of growth: Vigorous, sturdy shoots produced in moderate to high numbers.

Habit of growth: Spreading in young plants, later tending to become semi-erect. Side shoots usually absent.

Coloring: Dark green with anthocyanin pigments frequently intense.

Spines: Only moderately sized, dense, elliptical at their base and intensely pigmented (red) at base and tip. Triangulate and with short sharp tip.

Hairiness: Absent or weak.

Bloom: Weak.

Leaflets: Usually five, slightly convex on upper surface and touching each other.

Leaf color: Medium to deep green, frequently with red pigment, usually around margins.

Petiole: Medium length, frequently strongly red-tinged.

Terminal leaflet: Medium length; broad but longer than broad. Cordate base and flat tip.

Lateral leaflets: No stalklets present.

Leaf veins: Medium to strong relief between veins.

DESCRIPTION OF DORMANT CANES

Dormant canes densely spined, spreading or semi-erect, of medium diameter and long. The strong intensity of purple coloring is a characteristic feature of upper and lower parts, masking all green and secondary colors. Typical canes commonly are approximately 9 to 10 feet long.

DESCRIPTION OF FRUITING LATERALS, FLOWERS AND FRUITS

Fruits are well presented in fruiting laterals of about one foot length. They are typically deep red or purplish red and change to a deep purple when over-ripe, large and of long conical shape. The fruits of the present variety are darker than those of the Loganberry and tend to be more purple in color than those of the Loganberry which are more red in color. This color comparison is apparent from the following values obtained with the Gardner Colour Difference Metre in accordance with standard procedures:

| | L | a | b |
|---|---|---|---|
| Loganberry | +14.7 | +30.5 | +07.74 |
| Tayberry | +12.07 | +26.71 | +06.22 |

They have a slightly glossy appearance with only very slight downiness. They separate from the plant with the plug remaining attached. Ripening commences early and extends over a long period.

GENERAL DESCRIPTION

Fruiting laterals: Usually about one foot long.

Flower: Medium size with prominent conical receptacle.

Pedicel: Highly pigmented.

Fruit: Very large, deep red or purplish red and change to deep purple when over-ripe and long conical with high drupelet number. The fruit weight commonly ranges from approximately 5 to 5.5 grams during a dry season, and from approximately 7 to 11 grams during a wet season. Fruit dimensions commonly range from approximately 33 to 50 mm. (e.g., 39 mm.)×approximately 17 to 23 mm. (e.g., 20 mm.). There are typically from approximately 5 to 7 fruits per lateral (e.g., 6). The fruit is similar to that of the Loganberry with respect to juiciness.

Fruit quality: Medium firm, slightly glossy and highly flavored.

Plug: Large, long conical, separates with the fruit when picked.

Season of ripening: Early (equal to a mid-season raspberry) and extending over a long period.

Yield: Fruit yield per plant is influenced considerably by plant spacing. For plants spaced three feet apart in rows nine feet apart a typical yield is 3 to 3.5 kg. per plant during a dry season.

Disease resistance: Apart from crown gall (*Agrobacterium radiobacter* var *tumefaciens)*, no diseases or pests have been observed.

Storage capability: The storage capability of the fruit is comparable to that of the Loganberry. The fruit stores well when deep frozen.

I claim:

1. A new and distinct variety of hybrid Rubus substantially as herein shown and described.

* * * * *